US00PP24617P2

(12) United States Plant Patent
Smith

(10) Patent No.: US PP24,617 P2
(45) Date of Patent: Jul. 8, 2014

(54) ***CHRYSANTHEMUM* PLANT NAMED 'CIFZ0007'**

(50) Latin Name: *Chrysanthemum×morifolium*
Varietal Denomination: CIFZ0007

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 42 days.

(21) Appl. No.: 13/694,376

(22) Filed: Nov. 27, 2012

(51) Int. Cl.
*A01H 5/00* (2006.01)

(52) U.S. Cl.
USPC ..... Plt./288

(58) Field of Classification Search
CPC ..... A01H 5/0255; A01H 5/025; A01H 5/02; A01H 5/00
USPC ..... Plt./288
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0007' particularly distinguished by the medium sized white decorative inflorescences, medium green foliage color, medium to large rounded plant habit and a natural season flowering response of mid to late September.

1 Drawing Sheet

Latin name of the genus and species of the plant claimed: *Chrysanthemum×morifolium.*

Varietal denomination: 'CIFZ0007'.

BACKGROUND OF THE NEW PLANT

The present invention comprises a new *Chrysanthemum*, botanically known as *Chrysanthemum×morifolium*, and hereinafter referred to by the variety name 'CIFZ0007'.

'CIFZ0007' is a product of a planned breeding program. The new cultivar has medium sized white decorative inflorescences, medium green foliage color, medium to large rounded plant habit and a natural season flowering response of mid to late September.

'CIFZ0007' originates as a whole plant mutation of a parent plant designated as '05-M162'. 'CIFZ0007' was discovered and selected by the inventor in November 2008 as a single flowering plant within a large population of the parent cultivar grown in pots outdoors in Alva, Fla. The parent cultivar '05-M162' has light lavender inflorescence color.

The first act of asexual reproduction of 'CIFZ0007' was accomplished when vegetative cuttings were propagated from the initial selection in January 2009 in a greenhouse in Alva, Fla.

BRIEF SUMMARY OF INVENTION

Horticultural examination of plants grown from cuttings of the plant initiated in January 2009, and continuing thereafter, has demonstrated that the combination of characteristics as herein disclosed for 'CIFZ0007' are firmly fixed and are retained through successive generations of asexual reproduction.

'CIFZ0007' has not been observed under all possible environmental conditions. The phenotype may vary significantly with variations in environment such as temperature, light intensity, and day length.

Plant Breeder's Rights for this cultivar were applied for in Canada on Feb. 24, 2012 (12-7526) and at the Community Plant Variety Office on May 10, 2012 (2012/1026). 'CIFZ0007' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIFZ0007' with colors being as true as possible with an illustration of this type. The photographic drawing shows a flowering plant of the new variety, and a close-up of the inflorescences.

DETAILED BOTANICAL DESCRIPTION

The plant descriptions, measurements and aforementioned photographs were taken in Gilroy, Calif. in early August 2012 outdoors. These plants were about 12-14 weeks of age, grown in 1 gallon pots in an outdoor trial.

Color references are made to The Royal Horticultural Society Colour Chart (R.H.S.) 2001.

TABLE 1

DIFFERENCES BETWEEN THE NEW VARIETY 'CIFZ0007' AND A MOST SIMILAR VARIETY

| | 'CIFZ0007' | 'Yohelga' (U.S. Plant Pat. No. 13,811) |
|---|---|---|
| Blackcloth response: | About 1 week faster | About 1 week slower |
| Natural season response: | ½ week slower | ½ week faster |
| Plant size: | Little larger | Little smaller |
| Stem strength: | Stronger | Weaker |
| Ray floret color: | More white | More creamy |

Plant:
*Form, growth and habit.*—Herbaceous garden-type, stems upright and outwardly spreading, freely branching, strong and moderately vigorous growth habit.
*Plant height.*—15-17.0 cm.
*Plant height (inflorescence included).*—26-28.0 cm.
*Plant width.*—39-42.0 cm.

Roots:
*Number of days to initiate roots.*—About 4 days at about 22 degrees C.
*Number of days to produce a rooted cutting.*—4-6 days at 22 degrees C.
*Type.*—Fine, fibrous, free branching.
*Color.*—RHS N155B but whiter.

Foliage:
*Arrangement.*—Alternate.
*Immature, leaf color, upper surface.*—Darker than RHS 137A.
*Immature, leaf color, lower surface.*—Between RHS 137A and RHS 137B.
*Mature, leaf color, upper surface.*—Darker than RHS 137A.
*Mature, leaf color, lower surface.*—Between RHS 137A and RHS 137B.
*Length.*—3.7-4.3 cm.
*Width.*—3.6-4.0 cm.
*Shape.*—Ovate.
*Base shape.*—Attenuate.
*Apex shape.*—Mucronulate.
*Margin.*—Palmately lobed; irregularly incised, slightly serrulate.
*Texture, upper surface.*—Bifid T-shaped hairs.
*Texture, lower surface.*—Bifid T-shaped hairs.
*Color of veins, upper surface.*—RHS 146B.
*Color of veins, lower surface.*—RHS 146A.
*Pattern of veining.*—Palmate.
*Petiole color.*—RHS 146B.
*Length.*—1.6-1.8 cm.
*Diameter.*—0.2 cm.
*Texture.*—Bifid T-shaped hairs.

Stem:
*Quantity of main branches per plant.*—8-10.
*Color of stem.*—Closest to RHS 146A but appears lighter due to hairs.
*Length of stem.*—10-12.0 cm.
*Diameter.*—0.4 cm.
*Length of internodes.*—0.5-1.2 cm.
*Texture.*—Bifid T-shaped hairs.
*Color of peduncle.*—Closest to RHS 146A but appears lighter due to hairs.
*Length of peduncle.*—9-11.0 cm.
*Peduncle diameter.*—0.2 cm.
*Texture.*—Bifid T-shaped hairs.

Inflorescence:
*Type.*—Compositae, solitary decorative, inflorescences borne terminally above foliage, ray florets arranged acropetally on a capitulum.
*Quantity of short days to flowering (response time).*—About 46 days.
*Natural season flowering.*—Mid to late September.
*Quantity of inflorescences per plant.*—About 55 plus approximately 100 buds.
*Lastingness of individual blooms on the plant.*—Little longer than 6 weeks from first color.
*Fragrance.*—Slightly spicy.

Bud (just when opening/showing color):
*Color.*—RHS 4C.
*Length.*—0.6-0.9 cm.
*Width.*—0.8-1.0 cm.
*Shape.*—Oblate.

Immature inflorescence:
*Diameter.*—3.4-5.0 cm.
*Color of ray florets, upper surface.*—RHS 4D with RHS 6C apex.
*Color of ray florets, lower surface.*—RHS 4C.

Mature inflorescence:
*Diameter.*—6-6.3 cm.
*Depth.*—2.2-2.4 cm.
*Total diameter of disc.*—0.5 cm.
*Receptacle color.*—Closest to RHS 144B.
*Receptacle height.*—0.45 cm.
*Receptacle diameter.*—0.5 cm.

Ray florets:
*Average quantity of florets.*—175-200 in numerous whorls.
*Color of florets, upper surface.*—Closest to RHS 155D but more white with a small patch of RHS 144B basally.
*Color of florets, lower surface.*—Closest to RHS 155D but more white with a small patch of RHS 144B basally.
*Length.*—Mostly 2.3-2.5 cm with several closer to 2.7 cm.
*Width.*—Mostly 0.6-0.7 cm with several at 0.9 cm.
*Shape.*—Elliptical.
*Apex shape.*—Praemorse.
*Base shape.*—Attenuate.
*Margin.*—Entire.
*Texture, upper surface.*—Papillose.
*Textures, lower surface.*—Papillose.

Disc florets:
*Average quantity of florets.*—14-25.
*Color of florets.*—RHS 1C with RHS 9A apex.
*Length.*—0.4-0.5 cm.
*Width.*—0.1 cm.
*Shape.*—Tubular, elongated.
*Apex shape.*—Acute, 5 pointed.
*Texture, inner surface.*—Glabrous.
*Textures, outer surface.*—Glabrous.

Phyllaries:
*Quantity.*—About 40.
*Color, upper surface.*—RHS 138A.
*Color, lower surface.*—RHS 138A with RHS 137A margins.
*Length.*—0.7-0.9 cm.
*Width.*—0.15-0.2 cm.
*Shape.*—Lanceolate to linear.
*Apex shape.*—Acute.
*Base.*—Fused.
*Margins.*—Entire; with papery brown margins of about RHS 165A.
*Texture, upper surface.*—Glabrous.
*Textures, lower surface.*—Bifid T-shaped hairs.

Reproductive organs:
*Pistil.*—1, found on both types of florets.
*Length.*—0.5 cm.
*Style color.*—RHS 1C.
*Style length.*—0.4 cm.
*Stigma color.*—RHS 9A.

*Stigma shape*.—Bi-parted with a fuzzy apex.

*Ovary color*.—To this date is not mature enough to observe.

*Stamens*.—4, found only on the disc florets.

*Condition of stamens*.—To this date, stamens were observed, but were all completely dried up so as not able to observe color and measurements.

*Fertility/seed set*.—Has not been observed to date.

*Disease/pest resistance*.—Has not been observed to date.

What is claimed is:

1. A new and distinct variety of *Chrysanthemum* plant named 'CIFZ0007' substantially as illustrated and described herein.

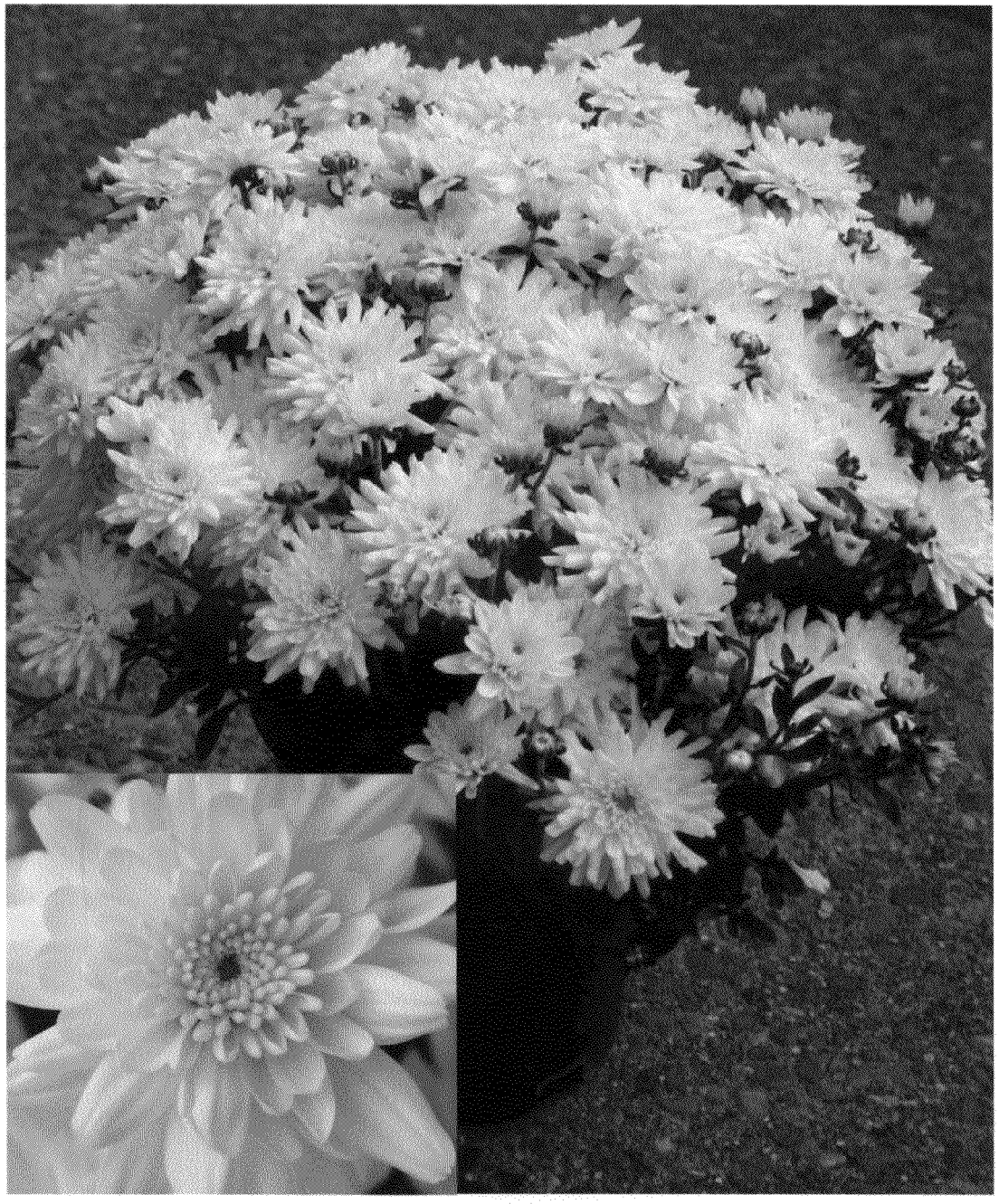

* * * * *